United States Patent [19]

Doucette

[11] Patent Number: 5,430,942
[45] Date of Patent: * Jul. 11, 1995

[54] SURGICAL BLADE HOLDER AND BLADE COMBINATION

[75] Inventor: Thomas H. Doucette, West Milford, N.J.

[73] Assignee: Becton Dickinson and Company, Franklin Lakes, N.J.

[*] Notice: The portion of the term of this patent subsequent to Dec. 28, 2010 has been disclaimed.

[21] Appl. No.: 124,122

[22] Filed: Sep. 20, 1993

Related U.S. Application Data

[60] Division of Ser. No. 944,857, Sep. 14, 1992, Pat. No. 5,272,812, which is a continuation-in-part of Ser. No. 645,387, Jan. 24, 1991, Pat. No. 5,146,685, which is a continuation-in-part of Ser. No. 612,356, Nov. 13, 1990, Pat. No. 5,060,387.

[51] Int. Cl.⁶ ............................................. B26B 1/00
[52] U.S. Cl. ........................................ 30/330; 30/335; 606/167
[58] Field of Search .................. 30/329, 330, 335, 346, 30/357, 339, 331; 606/167, 170

[56] References Cited

U.S. PATENT DOCUMENTS

| | | | |
|---|---|---|---|
| 1,261,815 | 4/1918 | Housdorfer | 30/335 |
| 1,554,083 | 9/1925 | Goldman | 30/339 |
| 1,823,001 | 9/1931 | Rassier | 30/331 |
| 1,914,153 | 6/1933 | Ogden . | |
| 2,064,176 | 12/1936 | Parker | 30/330 |
| 2,191,276 | 2/1940 | Gardner et al. | 30/330 |
| 2,708,313 | 5/1955 | Steele | 30/339 |
| 3,802,077 | 4/1974 | Averitt | 30/339 |

*Primary Examiner*—Richard K. Seidel
*Assistant Examiner*—Hwei-Siu Payer
*Attorney, Agent, or Firm*—Alan W. Fiedler; Eric M. Lee

[57] ABSTRACT

A combination surgical blade holder allows simple insertion sequentially of a plurality of blades, each blade having an opening for receiving a cleat and/or an abutment in a blade receiving area on the holder. The holder includes a fixed portion and a rotatable portion that pivot relative to one another in the same longitudinal plane around a pivot point positioned adjacent the blade receiving area and lock together to securely hold the blade in the blade receiving area. While the fixed portion of the holder is gripped in one hand, the thumb or finger of the same hand is used to unlock and rotate the rotatable portion to release and eject the blade single-handedly, without touching the blade. The fixed portion of the holder includes a cleat and/or an abutment that mate with an opening in the blade. Alternatively, the blade includes a tab that mates with a depression in the blade receiving area to lock the blade in the holder.

8 Claims, 9 Drawing Sheets

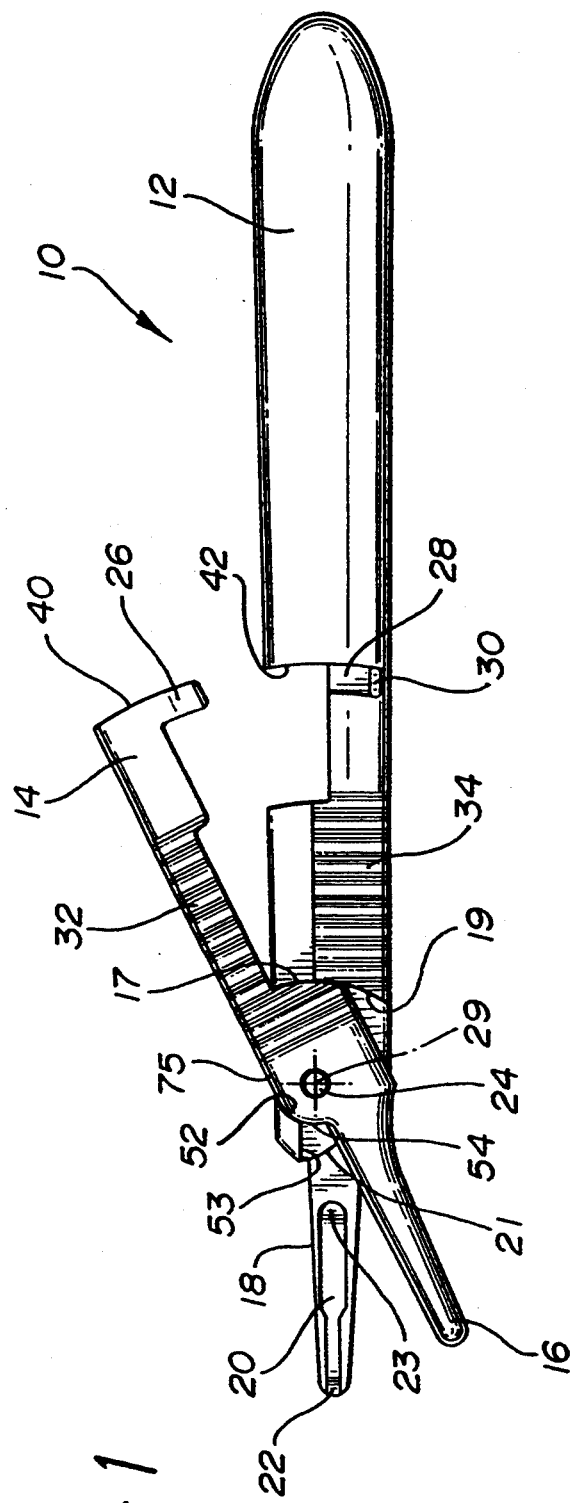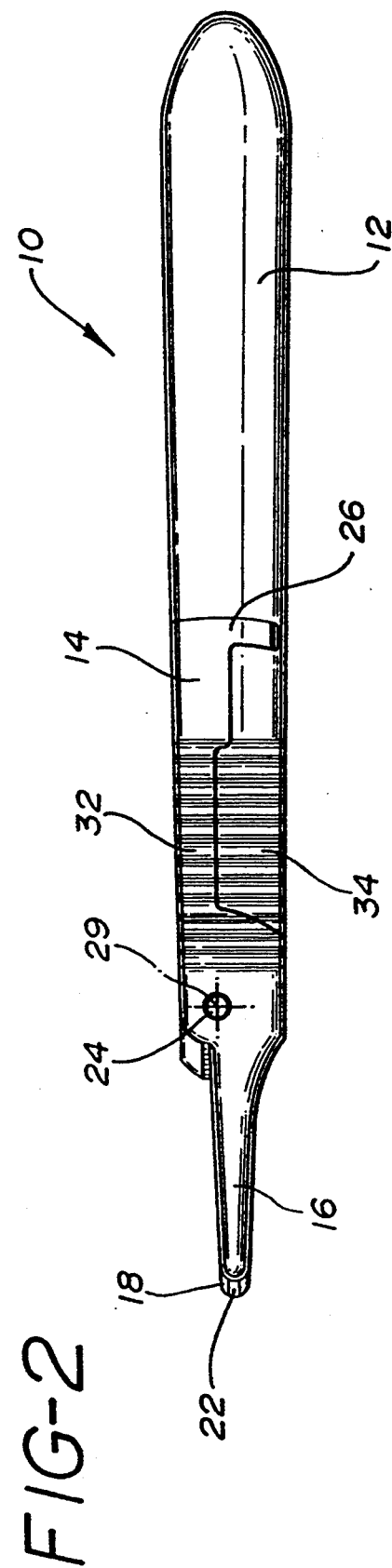

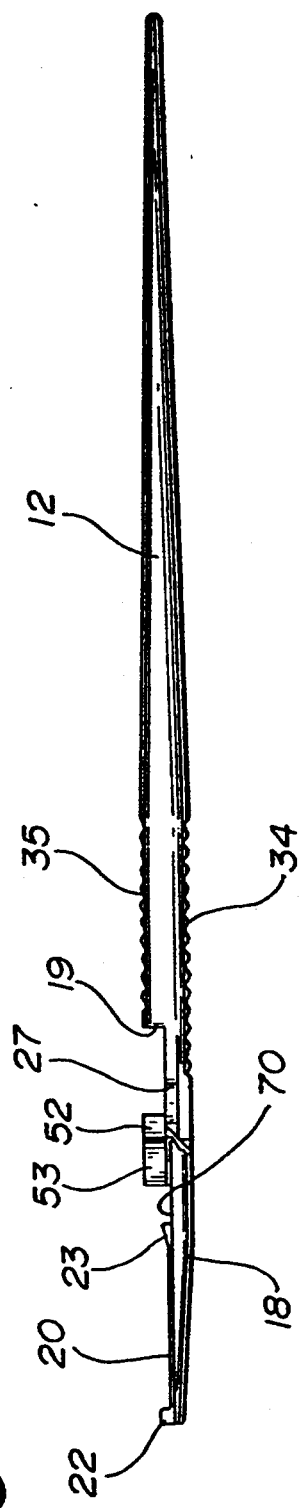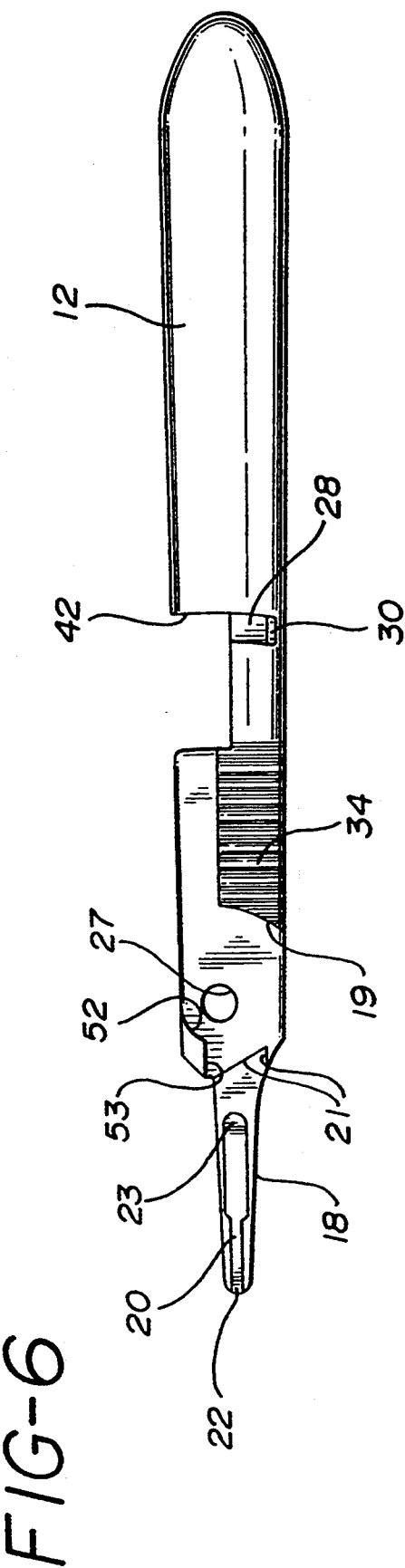

SURGICAL BLADE HOLDER AND BLADE COMBINATION

This application is a division of application Ser. No. 07/944,857, filed Sep. 14, 1992, now U.S. Pat. No. 5,272,812 which is a continuation-in-part of U.S. patent application Ser. No. 645,387, filed Jan. 24, 1991, now U.S. Pat. No. 5,146,685 which is a continuation-in-part of U.S. Pat. No. 5,060,387, issued Oct. 29, 1991, and based upon U.S. patent application Ser. No. 612,356, filed Nov. 13, 1990.

BACKGROUND OF THE INVENTION

1. Field of the Invention

The present invention relates to a blade handle or holder which allows for the sequential insertion of a plurality of blades for a single use of each blade with subsequent ejection of the blade from the handle for insertion of an additional blade. More particularly, the invention relates to holders for surgical blades of a precise configuration, and to the blades so configured. Also, this invention involves the handling of contaminated blades in the surgical environment.

2. Background Description

As practitioners-in-the-art of surgical blades are aware, AIDS, hepatitis and related contagious diseases present in the blood of patients have made the practice of surgery and medicine, in general, more dangerous than was the case several years ago, simply because one must be extremely careful to avoid contamination of his or her own blood with the blood of an infected patient. For this reason, many devices have been developed for handling instruments to avoid contaminated sharp edges or points which have been contaminated with the blood of infected persons. This is particularly true in the surgical environment where surgical blades are used in great quantity and must be disposed of without being touched, if possible, and certainly without the user being cut or having his or her skin punctured in any way.

Thus, it is important to be able to insert and remove a blade from a holder for the blade, without the user having to actually touch the blade, if possible. If it is necessary to touch the blade, then it is appropriate to touch only the tang portion of the blade and avoid any contact with the sharp edge. It is to this environment that the present invention is directed.

Many arrangements have been developed to obviate the problems discussed above, and to provide blade holders which will hold the blade precisely in the position desired, provide ease of insertion so that a user is not cut prior to any use of the blade and/or holder, and insure that the blade is firmly held against any wobbling or movement in the handle, which would reduce the effectiveness of any surgery being performed with such a blade.

Arrangements have been provided in the past wherein elongated blade holders have been provided with two parts of the holder pivoting relative to each other for insertion of the blade into the holder and for holding the blade in place. These arrangements have a pivot axis at one end of the two parts forming the holder. With such an arrangement, the user cannot perform removal of the blade single-handedly since it is necessary to use both hands for handling the two pivoting parts. Representative of such arrangements are U.S. Pat. Nos. 2,245,096 and 3,906,625. Both of these patents have the pivot axis positioned at the end opposite the end where the blade is inserted.

Other devices of the kind discussed herein include those in which the pivot axis is positioned centrally of the ends of the blade holder. Again, with such arrangements the user must use both hands to manipulate the two parts around the central pivot axis in order to insert and remove the brade. Representative of such prior art patents are U.S. Pat. Nos. 2,478,668 and 2,637,105.

In order to facilitate a single-handed operation for surgical blade holders and the cooperating blade of the kind discussed herein, the pivot axis is positioned adjacent to the blade during use. This enables the user to have a substantially long non-pivoting handle portion to grip for opening and closing the device for insertion and ejection of the blade. Representative of such arrangements are U.S. Pat. Nos. 2,039,443 and 1,914,153. Both of these patents use a separate rotating ejector arrangement which pivots adjacent to the blade to cause the blade to become "unwedged" from its use position for removal of the blade. However, the ejector cams the blade only partially out of its holder arrangement. The user must, after this camming action, grip the blade for final removal from the handle thus risking a cut from the contaminated blade.

SUMMARY OF THE INVENTION

With this invention, by contrast, a blade holder is provided for surgical blades which allows the user to open and close the device singlehandedly. The arrangement includes a fixed nonrotating half of the handle which has positioned in the blade position thereof a boss which is configured to be the same as the opening in the tang of the blade to be inserted. As a further feature, this portion of the holder is indented to the same configuration as the blade tang for easy reception of the blade. For this reason, the blade may be positioned on the fixed portion of the handle of the invention.

At one end of the boss is a cooperating abutment which cooperates with the movable portion of the handle in closed position to capture the blade and lock it in a non-movable position for use. The other end preferably includes a hook or cleat arrangement with an undercut surface that serves to positively position and hold one end of the blade. The opposed half of the blade holder preferably includes a distal or nose end that fits under the undercut of the cleat with the blade therebetween. Thus, the user, single-handedly, may close the device and wedge the blade in a fixed position effortlessly.

It is equally important in the surgical environment to have the blade held in a holder against any movement relative to the holder. This invention is directed to blades modified to accommodate a specifically configured holder for this purpose, the holders, and the combination of holder and blade. The holder preferably includes opposed cooperating surfaces which capture the blade in three dimensions, so to speak, against any movement in the holder with the blade being configured to meet precisely these opposed cooperating surfaces.

As a further feature of the holder portion of the combination in accordance with this invention, both portions of the holder preferably include wedge features which mate in closed position to hold the ribbed edge of the blade of the invention. The blade portion of the combination herein preferably includes an opening of expanded width at one end to cooperate with the cleat on the holder. Also, at the very distal end of the expanded width opening is an extension in the hole of the blade which cooperates with a front or distal end of the cleat.

Once the blade has been used, the user may grip the handle, and with the thumb, move the movable portion of the handle open around the pivot axis which is adjacent to the blade. In doing so, the user also places the boss side of the fixed portion of the handle downwardly. For this reason, once the movable portion of the blade handle has been forced open by the thumb of the user, the blade simply falls out of the device into a container used for such purposes in order to contain contaminated sharp instruments. The user does not touch the blade at all once it has been used and contaminated.

As a further preferred feature, the blade holder is substantially flat and the two portions of the handle pivot relative to one another around a pivot with an axis perpendicular to the flat body of the holder, and positioned adjacent to the position of the blade, as discussed above. Moreover, the two portions pivot around this pivot axis in substantially the same longitudinal plane relative to each other. For this reason, the profile of the holder herein is a simplified flat device easily handled and maneuvered in difficult surgical procedures.

Other preferred devices include different types of blade receiving areas and locking mechanisms. For example, a blade receiving area with a cleat and an abutment that are not connected to each other by a boss so that only the cleat and abutment are received in an opening in a blade and a locking mechanism having a channel on the fixed handle portion that receives a slanted protrusion on the rotatable handle portion when the device is in a closed position.

Another preferred device is capable of receiving the blade in the blade receiving area while the device is in the closed position, wherein a tab of the blade is locked into a depression in the fixed handle portion or a slanted abutment engages with an opening in the blade to lock the blade in the device.

In addition, other objects and advantages of the present invention will be apparent from the following description, the accompanying drawings and the appended claims.

DESCRIPTION OF THE DRAWINGS

FIG. 1 is a longitudinal side elevational view of a preferred device of the invention in its open position exposing the boss structure for receiving a surgical blade;

FIG. 2 is the structure of FIG. 1 shown in its closed position;

FIG. 5 is a longitudinal end view of the fixed portion of the handle of the invention;

FIG. 6 is a side elevational view of the fixed portion of the handle of the invention of FIG. 5 with the rotating portion removed to show the structure of the fixed portion underneath the rotating portion;

DETAILED DESCRIPTION

Figure 3:
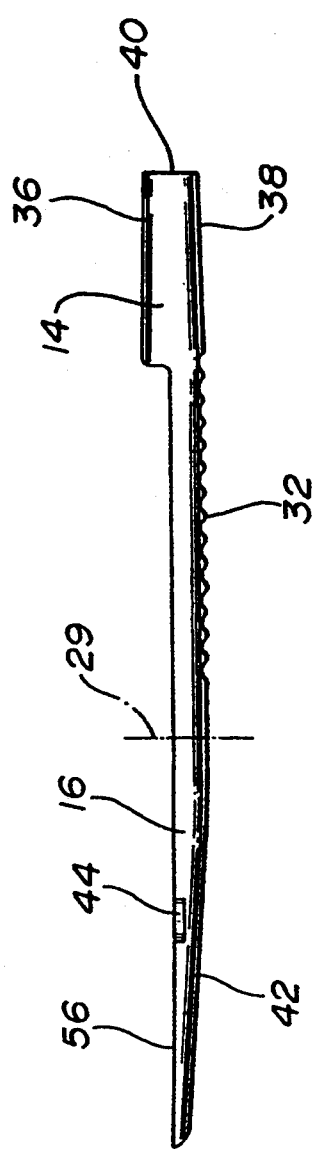
FIG. 3 is a longitudinal end view of the movable handle portion of the holder of the invention.

Referring to the drawings in which like reference characters refer to like parts throughout the several views thereof, FIG. 1 shows one embodiment of the surgical blade holder of the invention generally designated 10 in its open position with a fixed handle portion 12 and a rotating handle portion 14. Two halves 12 and 14 rotate relative to each other around a pivot axis 29 with a pivot pin 24 for that purpose. In use, however, the smaller half 14 rotates while portion 12 is held, and therefore, fixed.

Front end portions 16 and 18, respectively, of the blade holder halves 14 and 12, when open, expose a boss 20 having abutments 22 and 23 positioned at each end thereof. Boss 20 is configured to be the same as a conventional opening in the tang of a conventional surgical blade for holding the blade in a fixed position once the two portions of the holder 10 are in their closed position as shown in FIG. 2. L-shaped surface 21 (FIG. 6) defines the rear end of the indentation in portion 18 for receiving the blade body.

That is, front end portion 16 of the blade holder movable half moves over the blade itself and boss 20 to wedge and position both between the two front halves 16 and 18 of blade holder 10. When this takes place, of course, abutments 22 and 23 provide a wedging action to hold the blade in a fixed non-moving position. In order to provide the appropriate rotating movement around axis 29, the movable and fixed portions 14 and 12 of the blade holder of the invention include cooperating opposed curved surfaces 54, 52, 17 and 19. This allows for rotation of the parts relative to each other without any diversion from the desired controlled rotary movement around pivot axis 29 and rotating pin 24.

Figure 4:
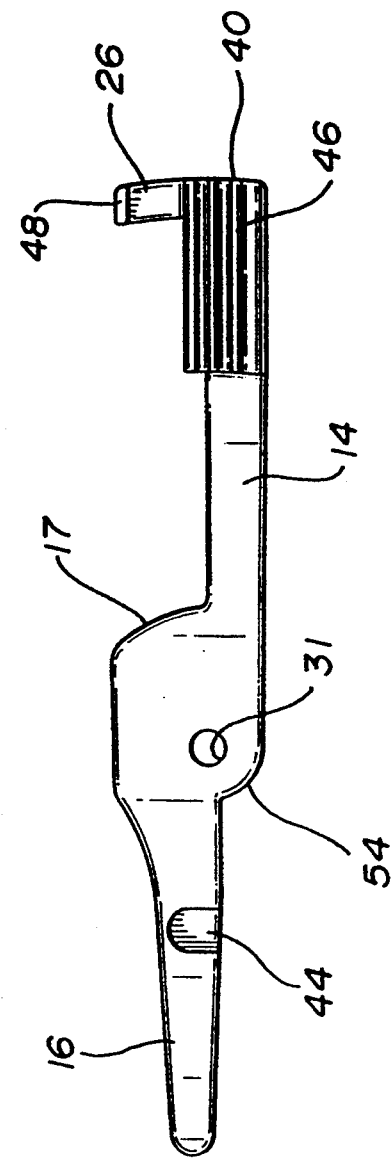
FIG. 4 is a side elevational view of the movable handle portion of the holder of the invention of FIG. 3 showing the opposite side thereof from the illustrations in FIGS. 1 and 2.

As can be seen in FIGS. 1 and 4, movable rotating portion 14 of handle 10 includes a locking extension 26 which is received in a slot 28 in the fixed portion 12 of handle 10. When extension 26 moves into slot 28, there is positioned at the bottom of extension 26 an abutment 48, which cooperates with a depression 30, so that 48 snaps in place locking the two parts against relative rotary movement when not desired.

Two halves 12 and 14 also include cooperating curved surfaces 42 and 40, respectively, again for maintaining a proper relative movement of the two parts around axis 29 and pivot pin 24. Flat surfaces of the movable and fixed parts 14 and 12 of the handle include a plurality of spaced vertical ridges 32 and 34 which serve to provide the user with a frictional gripping surface during use of the holder, when a blade is fixed in the holder. While cooperating curved surfaces 52 and 54 move relative to each other, in the complete open position of FIG. 1, top surface 75 of the movable part 14 moves against the top edge of surface 52 to serve as a stop against further opening movement.

Referring now to FIGS. 3 and 4, these views show the movable portion 14 of the blade holder of the invention separated from the fixed portion thereof for clarity. As can be seen in FIG. 4, this view is the opposite side of portion 14 from that of FIGS. 1 and 2, and 14 includes a plurality of spaced frictional ridges providing a frictional gripping surface 46. This surface serves to provide the user with a frictional surface for the thumb or finger for the opening movement necessary to open the device to allow the blade to drop from the open blade holder 10. Surface 56 on the front end portion of the blade half 14 preferably includes an opening 44 which cooperates with abutment 23 on the fixed portion of the device for maintaining the blade fixed between the cooperating surfaces of the fixed and rotating halves of holder 10 of the invention.

One of the features of the invention is the fact that the front portion 16 from the pivot axis 29 as shown in FIG. 3 is bowed slightly along the surface 56 to provide a more firm cooperating wedging action between surface 56 and the cooperating surface on the other half 12 of the blade holder 10 of the invention. Both the fixed and rotating halves of the blade holder of the invention include beveled edges 36 and 38, which provide a further ease of holding and/or gripping the holder of the invention during use. Finally, referring to FIG. 3, the movable half 14 of the holder of the invention includes a bore 31 for receiving the rotating pivot pin 24.

Referring now to FIGS. 5 and 6, the fixed half 12 of the holder 10 of the invention is shown separately from the movable half thereof. As can be seen in FIGS. 5 and 6, bearing surfaces 52 and 53 are shown for cooperating with opposed surfaces on the movable half 14 of the blade 10 of the invention. Surface 53 serves as a "stop" for movement to the closed position of the part 14 in cooperation with the movement of the abutment 48 into depression 30 to cause locking together of the two halves once the blade is in place between the two halves.

Referring now to FIG. 5, the front end portion 18 is bowed slightly as discussed above relative to surface 56 on rotating or movable portion 14 so that surface 70 cooperates with the opposed surface 56 in a wedging action. This bow may not be visible to the human eye since the degree of bow is very small in order to provide appropriate movement of the two parts together, and movement to a non-locking position when required to eject the blade. Fixed blade holder half 12 also includes a bore 27 for receiving the pivot pin 24 as discussed above. The fixed blade holder half 12 includes vertical ridges 34 and 35, as viewed in FIGS. 5 and 6, on opposite sides thereof in order to provide the user with a frictional surface for ease of holding the holder 10 during use.

Thus, in order to use the device 10 of the invention, the user grips the proximal end of the fixed portion 12 of the invention. For this purpose, as will be readily seen in FIGS. 1 and 2, a large portion of the elongated device of the invention is removed from any movable part so as to provide a gripping surface for opening and closing the device of the invention. Thereafter, the user places a thumb or finger against the surface 46 to provide a force for opening the movable portion 14 of the invention to expose the boss 20 and opposed locking wedges 22 and 23 for receiving the opening of a tang of a blade selected for insertion into the holder 10. The force for opening overcomes the cooperating locking surfaces of parts 48 and 30 of the two halves of the holder of the invention.

Once the holder has been opened, the user may place the blade appropriately with the opening of the blade over the boss 20. Then, the user simply moves the movable holder portion 14 so as to cause the abutment 48 to move in position in the depression 30 for locking the two parts together. With this movement, the blade is fixed in place with no "wobbling" in the holder. Then the user may use the holder with the blade in an appropriate desired way.

Subsequent to use, the contaminated blade may be removed readily by the user. This is done simply by, again, holding the prioximal end of the fixed portion 12 of the device 10 of the invention and placing the thumb or finger against the frictional surface 46 for movement of the rotating portion 14 around pivot axis 29. This force overcomes the locking engagement of cooperating parts 30 and 48 and allows the two parts to open to a position as shown in FIG. 1. Thereafter, the user may, if the boss 20 is positioned upwardly, simply turn the holder so that the boss is positioned downwardly and the blade will fall out into a container provided for that purpose.

For this reason, the user's hands are not contaminated by any blood on a blade which has been used in the holder of the invention. There is no required movement on the part of the user of any kind to touch or remove the blade from the holder. It simply falls from the holder when the holder is opened, as discussed above.

Figure 7:
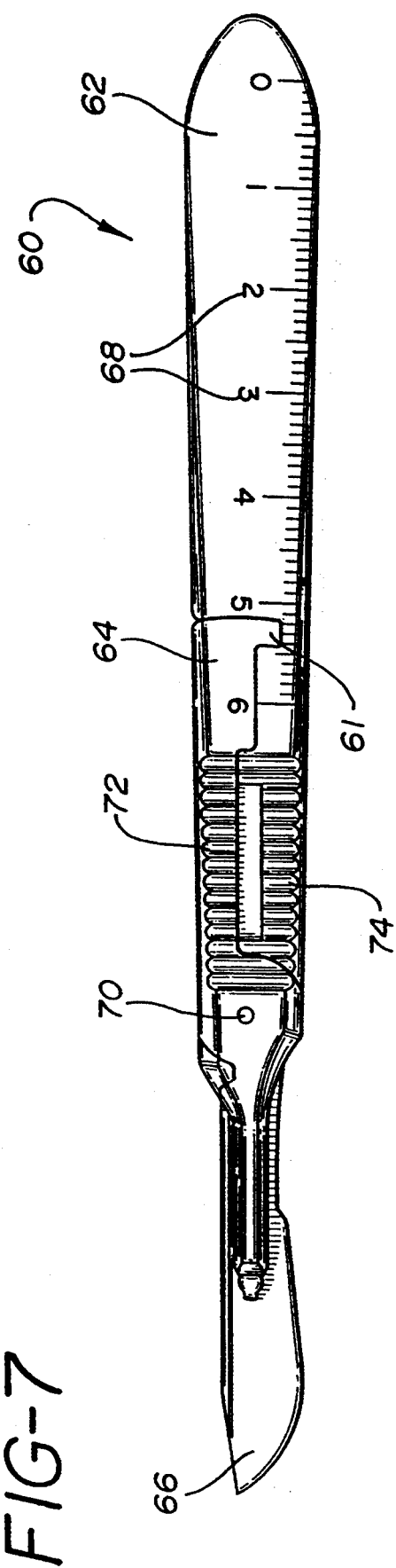
FIG. 7 is a longitudinal side elevational view of another embodiment of a prefered device of the invention illustrating the combination blade holder and blade with cooperating interfitting surfaces.
Figure 8:
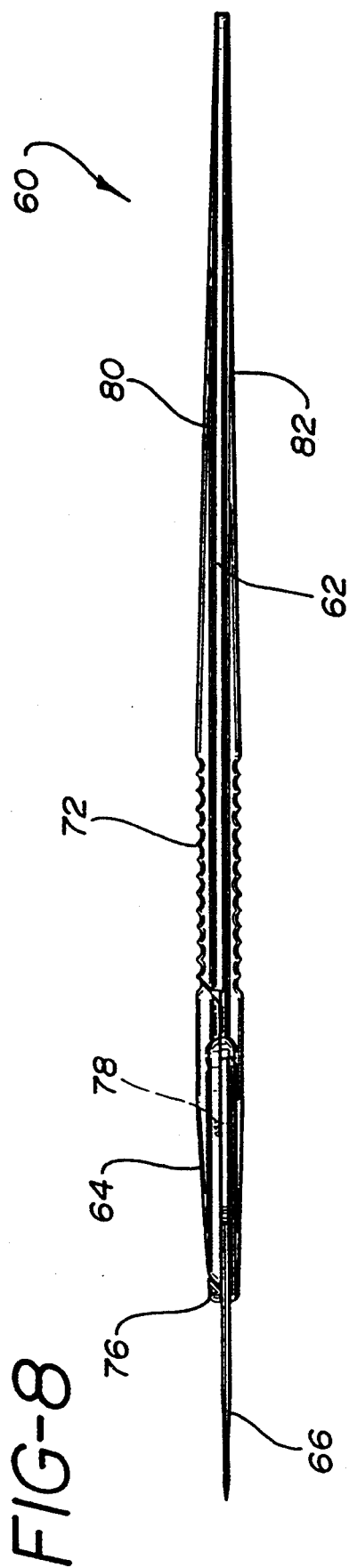
FIG. 8 is a longitudinal edge view of the device of FIG. 7 showing the bottom edge as viewed in FIG. 7.

FIGS. 7 and 8 show another embodiment of a surgical blade holder 60. In this embodiment, a combination blade and holder are provided in which both the blade and the holder have specifically configured cooperating surfaces to hold the blade fixed in the holder in an appropriate fashion. The holder is so configured that only blades with an opening configured in accordance with this invention will hold the blade. The embodiment shown in FIGS. 7 and 8 has a rotating and a fixed half 64 and 62, respectively, in the same manner as the embodiment shown and described in FIGS. 1-6. The two halves rotate around a pivot axis 70 in the same manner. Moreover, the smaller rotating half has a locking tab 61 in the same manner as the embodiment shown and described in FIG. 1.

Figure 9:
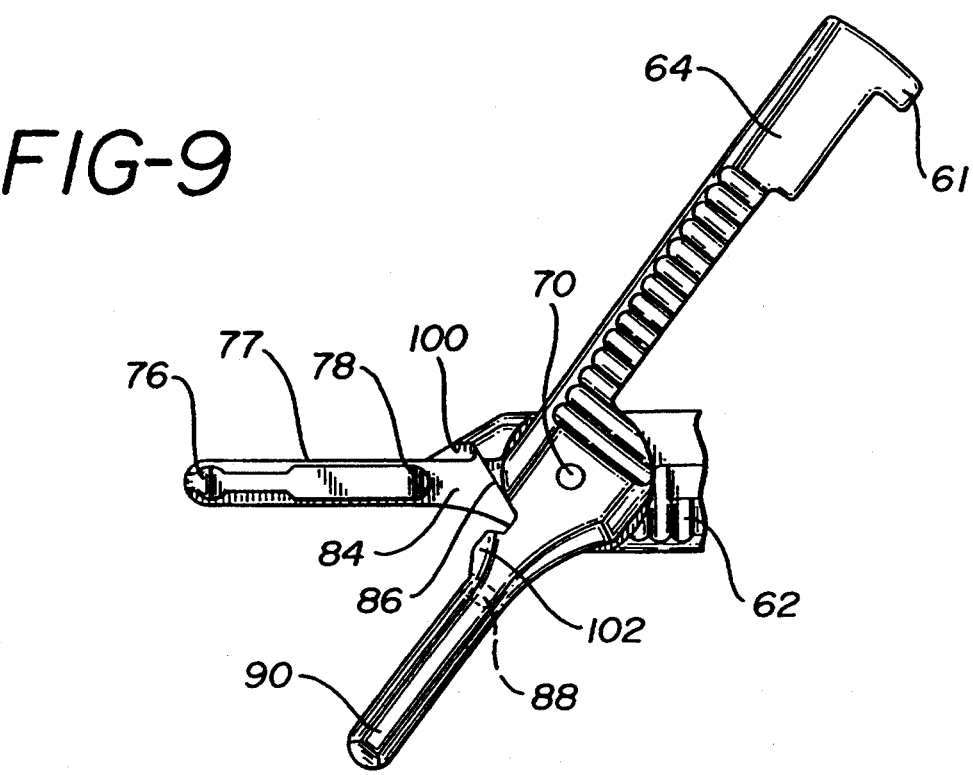
FIG. 9 is a partial longitudinal view of the device of FIG. 7 shown in open position, and showing the cooperating surfaces for the blade with the blade removed.

The difference lies in the specific blade opening boss configuration including a cleat 76 and abutment 78 spaced apart to cooperate with a specific opening configuration in the blade 66 of the invention. As shown in FIG. 8, the spaced apart abutment 78 and cleat 76 are positioned on the fixed longer portion 62 of the holder 60 of the embodiment of FIGS. 7 and 8. Further as shown in FIG. 7, the fixed portion 62 of the holder 60 includes measurements 68 which are utilized by the surgeon during surgery for measuring the dimension of an incision made by blade 66. As shown in FIG. 8, further, this embodiment 60 of the invention also includes beveled edges 80 and 82 and the cooperating textured surfaces 72 and 74 to assist in holding the holder 60 of the invention in a precise manner during surgical procedures Referring now to FIGS. 9 and 13, the specific boss configuration of the fixed portion 62 of holder 60 is shown with the spaced apart cleat 76 and abutment 78. As can be seen in FIG. 9, a specific mating feature 100 on the fixed portion of the holder 60 and 102 on the movable portion 64 cooperate with each other to grip rib back 114 of the blade 66. Because of this, rib back 114 of blade 66 is securely captured in both halves of the handle and serves to increase the secure three dimensional stability of the blade in the holder of the invention.

As can be seen in FIG. 9, further, distal end 90 of the movable portion 64 of the invention includes an opening 88 for receiving therein the abutment 78 on surface 84 in the closed position of holder 60.

Figure 10A:
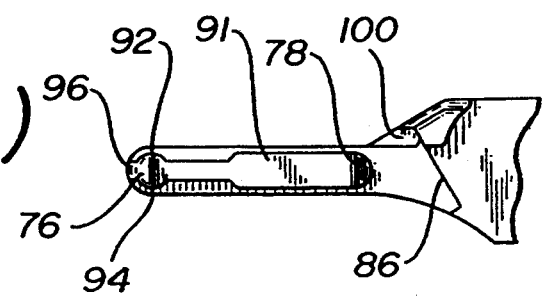
FIG. 10(a) is a partial longitudinal view of the long fixed handle portion of the blade holder showing the blade mating surface details.
Figure 10B:
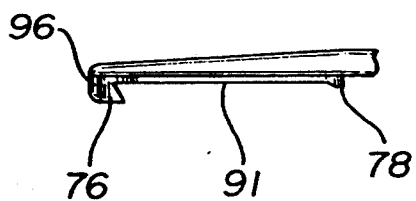
FIG. 10(b) is a side elevational view of blade holder portion of FIG. 10(a)
Figure 11:
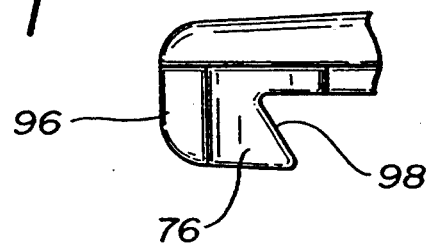
FIG. 11 is an enlarged partial view of FIG. 10(b) showing details of the cleat on the holder of the invention for cooperating with the opening in the blade of the invention.

Referring now to FIGS. 10(a) and 10(b), boss 91 includes the distal cleat 76 which has a forward extension 96. Cleat 76 extends on each side to points 92 and 94 for cooperating with the mating surfaces of blade 66, as will be described in more detail below. As can be seen in FIG. 11, in the enlarged view of cleat 76, the cleat has an overhang surface 98 which serves to lock the blade in place and for cooperating with the distal end of the opening of blade 66 which opening is specifically configured to cooperate only with the holder 60 described herein.

Figure 15:
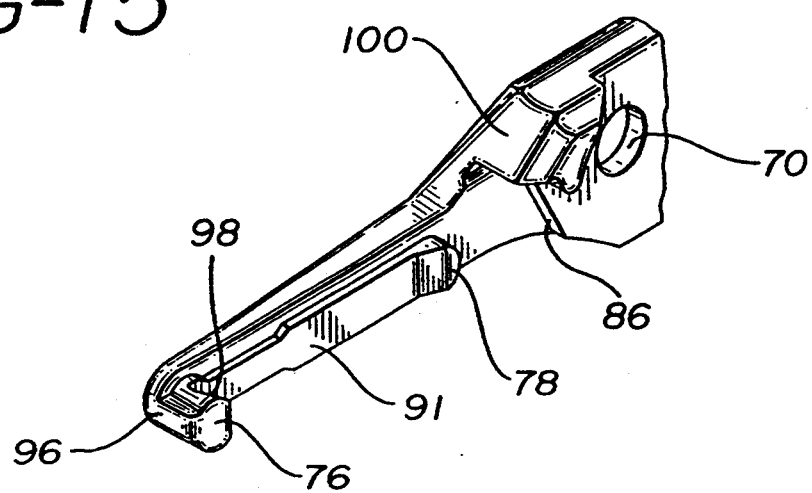
FIG. 15 is an isometric view of the blade receiving boss on the long handle portion of a prefered holder of the invention.

Prior to describing the configuration of the blade of the invention, reference is made to FIG. 15 which shows an isometric or perspective view of distal end 77 of the fixed portion 62. As can be seen in FIG. 15, boss 91 is configured for receiving a specific blade opening and shows the spaced apart abutment 78, cleat 76, as well as the rear mating surface 86 for receiving a proximal end 110 of blade 66. Also, the view in FIG. 15 shows the surface 100 for cooperating with surface 102 for engaging ribbed portion 114 of blade 66.

A Blade

Figure 12:
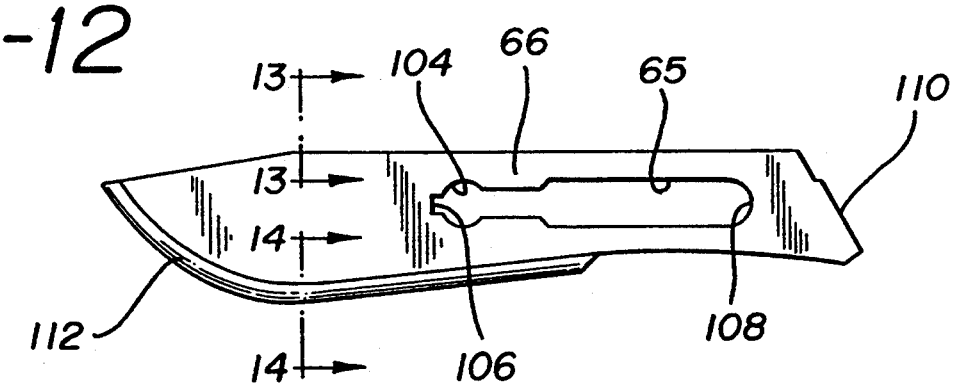
FIG. 12 is a plan view of a prefered blade of the invention.
Figure 13:
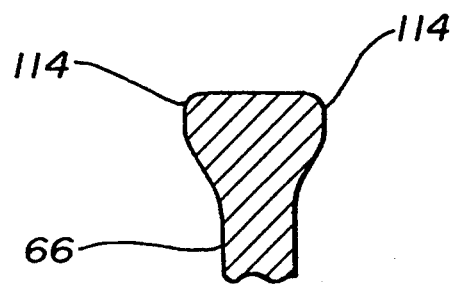
FIG. 13 is a sectional view along lines 13—13 of FIG. 12.
Figure 14:
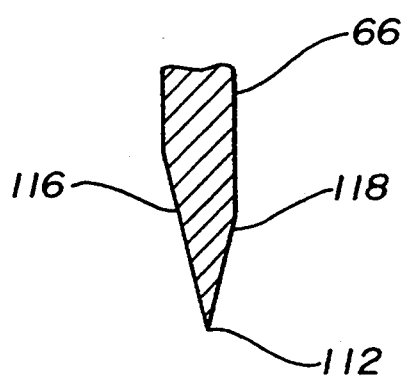
FIG. 14 is a sectional view along lines 14—14 of FIG. 12.

Referring now to FIGS. 12, 13 and 14, blade 66 of the invention is shown. As can be seen in FIG. 12, blade 66 has a specifically configured opening 65 with the proximal end of opening 65 being 108 for engaging abutment 78. However, as shown in FIG. 12, the distal end of opening 65 is configured substantially differently from conventional blade openings for surgical blades. That is, the distal end includes an enlarged round-shaped opening 104 for receiving and engaging cleat 76 with the distal extension 106 for receiving the extension 96 of cleat 76. Because of the undercut or overhang surface 98 of cleat 76, the blade is held in a more substantial position between the two halves of the holder 60 when the holder is in its closed position.

FIG. 13 shows a sectional view of ribbed portion 114 on the top surface of blade 66. FIG. 14 shows the opposed tapers 116 and 118 of blade 66 forming cutting edge 112 of blade 66.

Thus, as will be appreciated from the above, there is provided in accordance with this invention two forms of surgical blade holders which are relatively simple and uncomplicated in construction and easily stamped from a selected material such as stainless steel in a mass production line. In both arrangements, the user may insert a blade in a very simple manner and, again remove the blade without ever touching the blade if it should be in fact contaminated. It should be understood, of course, that one embodiment of a holder of the invention may be used for blades other than surgical blades, or with conventional surgical blades. The simplicity of the structure is such that many uses may be provided with the holder of the type described. However, it is also important to note that the holder of the invention, regardless of its simplicity, holds the blade in a complete fixed position with no movement in the holder. This allows the user to provide a precise cutting action as desired for the use of the blade being selected.

While the holder configured to fit the specific blade of the invention here is also easily stamped from stainless steel, for example, and may be easily loaded and unloaded with the blade of the invention, it has surfaces specifically configured on each half thereof to mate with the specific blade configuration of the invention.

Again, while the blade of the invention is simple to use and to manufacture, it has been developed with precisely arranged surfaces for three dimensional mating with the holder in accordance herewith. Because of this the blade is fixed from movement in any dimensional direction of its position in the cooperating holder.

An Alternative Blade Receiving Area

Figure 16:
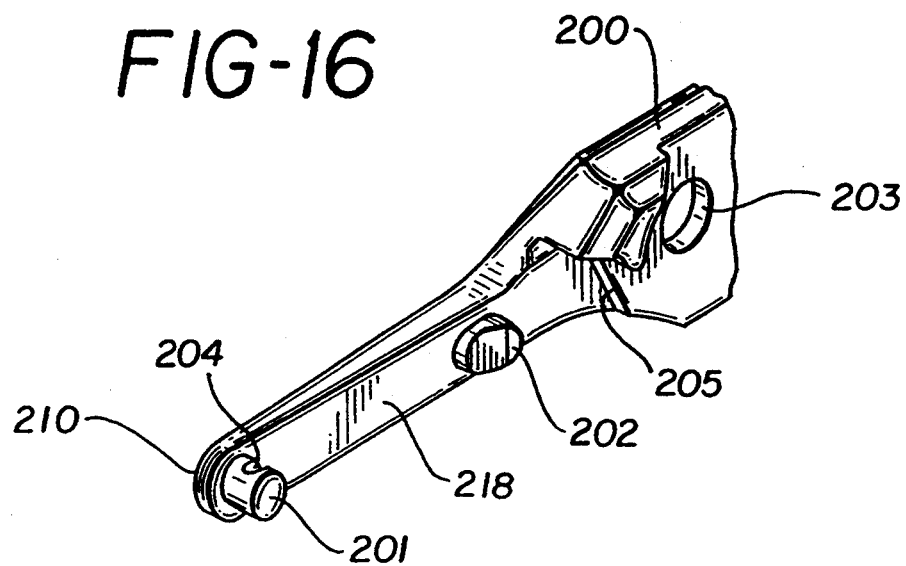
FIG. 16 is an isometric view of a blade receiving area on a fixed handle portion of a prefered holder of the invention.

FIG. 16 shows an isometric or perspective view of a blade receiving area 218 on a fixed handle portion 200, blade receiving area 218 being configured to receive blade opening 65 in blade 66 (FIG. 12).

As shown in FIG. 16, blade receiving area 218 includes a cleat 201 that is positioned at a distal end 210 of fixed handle portion 200 and an abutment 202. Cleat 201 and abutment 202 are spaced apart from each other and do not have a raised boss portion therebetween, and are received by enlarged round-shaped opening 104 and proximal end 108, respectively, in blade opening 65. In contrast to boss 91 shown in FIG. 15, only cleat 201 and abutment 202 extend through blade opening 65 when blade 66 is placed on blade receiving area 218.

An overhang surface 204 in cleat 201 aides in securing blade 66 between fixed handle portion 200 and a rotatable handle portion (not shown), when the rotatable handle portion has been rotated about pivot axis 203 and is in a closed position with respect to fixed handle portion 200. In the closed position, overhang surface 204 mates with the distal end of the rotatable handle portion to lock the blade in place, as described above with respect to FIGS. 9-11 and 15. In addition, a rear mating surface 205 is provided on fixed handle portion 200 for receiving and mating with proximal end 110 of blade 66.

Figure 17:
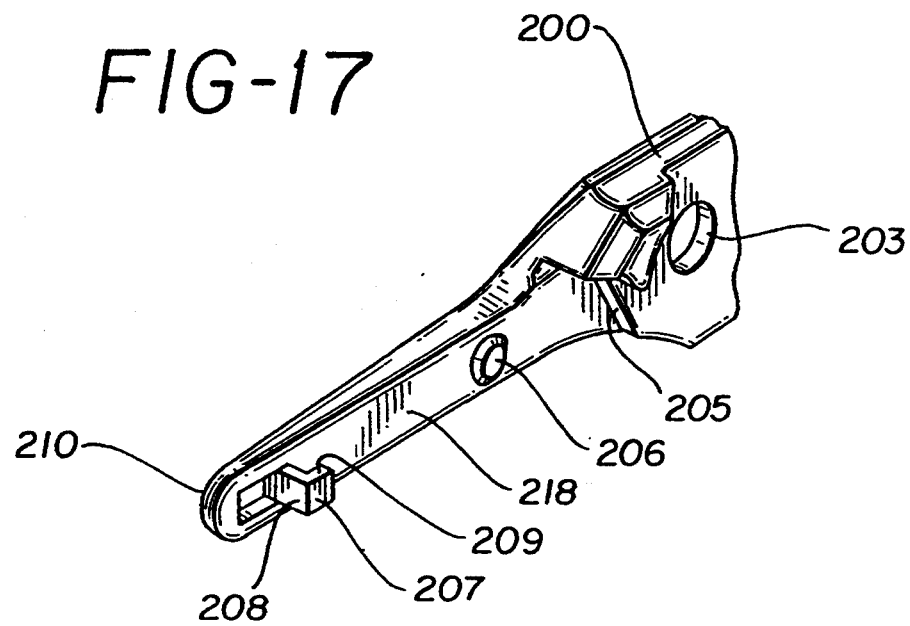
FIG. 17 is an isometric view of another blade receiving area on a fixed handle portion of a prefered holder of the invention.

The embodiment shown in FIG. 16 may be manufactured by casting or molding the handle portions, while the embodiment shown in FIG. 17 may be manufactured from formed steel or by a stamping process. FIG. 17 shows a blade receiving area 218 on fixed handle portion 200 having a cleat 207 spaced apart from a coin shaped abutment 206. Cleat 207 includes a leg 208 extending from distal end 210 and an arm 209 extending from the end of leg 208 in the proximal direction of fixed handle portion 200 to form an overhang structure. The overhang structure provides for securing blade 66 between fixed handle portion 200 and the rotatable handle portion, when the rotatable handle portion has been rotated about pivot axis 203 and is in a closed position. FIG. 17 also shows rear mating surface 205 for receiving proximal end 110 of blade 66.

The operation of the blade holders shown in FIGS. 16 and 17 is similar to the operation of the other blade holders described above.

A Further Embodiment

Figure 18:
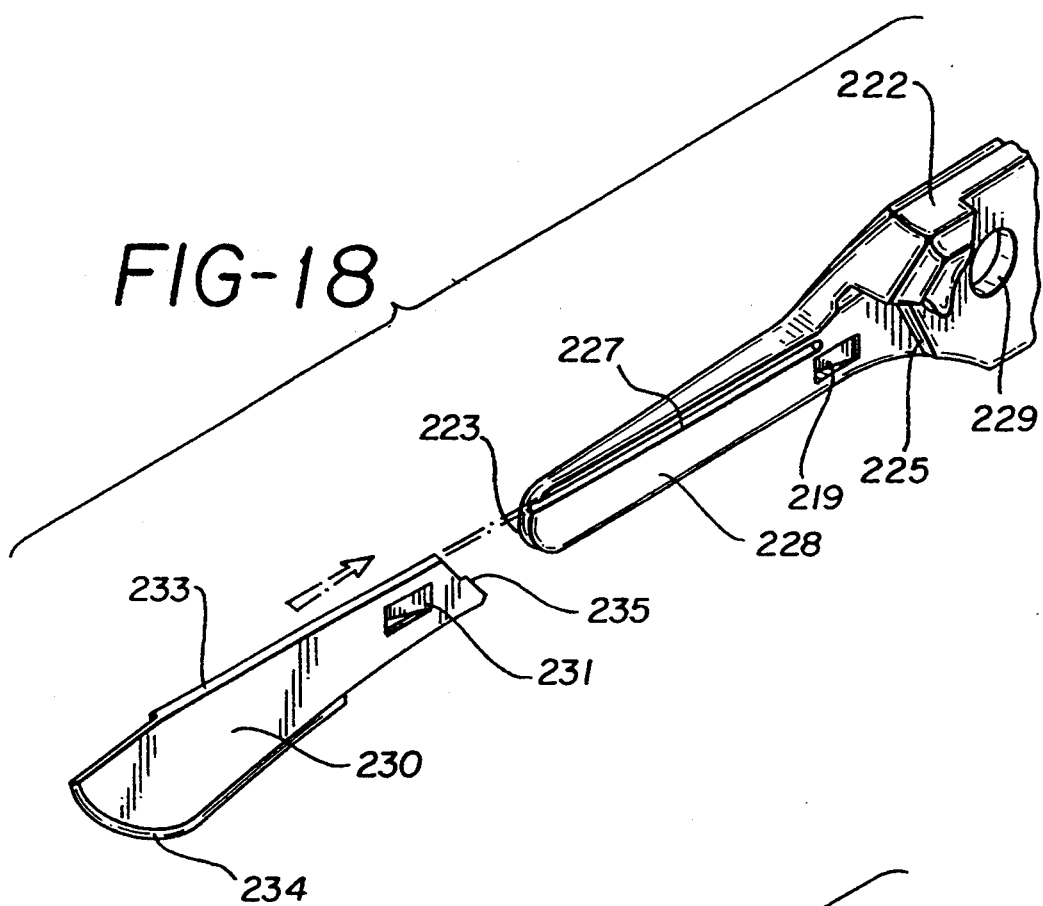
FIG. 18 is an exploded isometric view of a prefered holder of the invention showing a blade with an opening and a cooperating blade receiving area on a fixed handle portion.
Figure 19:
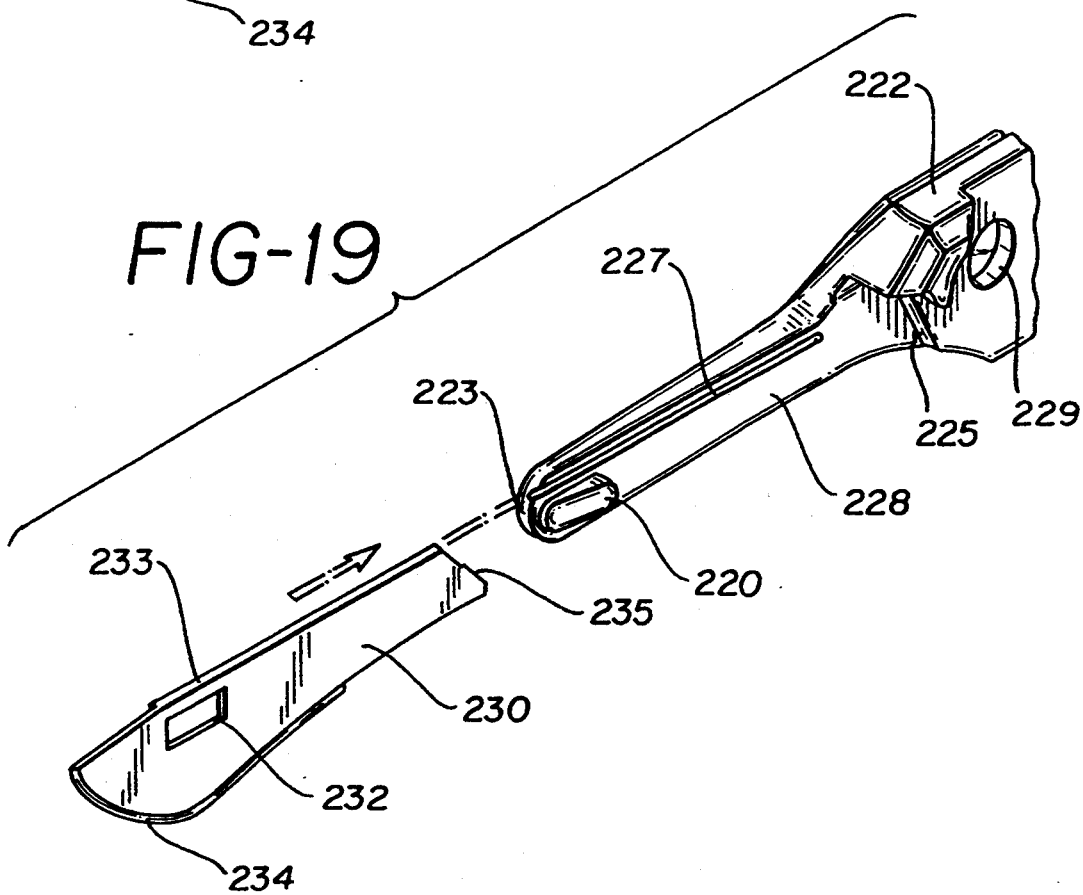
FIG. 19 is an exploded isometric view of a prefered holder of the invention showing a blade with a tab and a cooperating blade receiving area on a fixed handle portion.

FIGS. 18 and 19 are exploded isometric views of a further embodiment of a surgical blade holder of the invention showing a blade 230 and a cooperating blade receiving area 228 on a fixed handle portion 222. The rotatable handle portion is not shown so that blade receiving area 228 can be seen more clearly. In this embodiment, blade 230 is loaded into the holder with the fixed and rotatable handle portions in the closed position. Therefore, blade 230 can be slid, for example, from a blade dispensing device, between the distal ends of the fixed and rotatable handle portions and locked in place using one of the arrangements described below or equivalents thereof.

One such locking arrangement is shown in FIG. 18, wherein blade 230 includes a cutting edge 234 surrounding the distal end of the blade, a tab 231 projecting from the surface of the blade, and a rib 233 extending between the distal end of the blade towards proximal end 235 of the blade. Distal end 223 of fixed handle portion 222 also includes a pivot axis 229 about which a rotatable handle portion (not shown) rotates to permit the holder to move between an opened position and a closed position. As shown in FIG. 18, blade receiving area 228 at distal end 223 includes (i) a slanted depression 219 in the proximal end of blade receiving area 228 for receiving tab 231 on blade 230 and (ii) a groove 227 that extends from distal end 223 towards the proximal end of blade receiving area 228 for receiving rib 233 on blade 230. Fixed handle portion 222 also includes a rear mating surface 225 that engages with proximal end 235 of blade 230, when blade 230 is fully mounted in blade receiving area 228.

As blade 230 is being mounted in the holder shown in FIG. 18, with the fixed and movable handle portions in the closed position, rib 233 slides in groove 227 until tab 231 is received by depression 219 and proximal end 235 of blade 230 mates with rear mating surface 225. When tab 231 mates with depression 219 the blade is locked in the holder and thereby secured in three-dimensions. In addition, tab 231 on tang of blade 230 permits a user to easily pick up blade 230 from a flat surface, if necessary, without having to touch cutting edge 234.

The holder and blade arrangement shown in FIG. 19 is substantially similar to the arrangement shown in FIG. 18. However, tab 231 and depression 219 in FIG. 18 have been replaced with an opening 232 in blade 230 and a slanted abutment 220 at distal end 223 of fixed handle portion 222.

More specifically, FIG. 19 shows blade receiving area 228 on fixed handle portion 222 including (i) slanted abutment 220 which receives opening 232 in blade 30 and (ii) groove 227 extending between distal end 223 to the proximal end of blade receiving area 228 which receives rib 233. As with the arrangement shown in FIG. 18, when blade 230 is being mounted in the holder, rib 233 slides in groove 227 until proximal end 235 of blade 230 mates with rear mating surface 225. In the present arrangement, however, slanted abutment 220 is received by opening 232 in blade 230 to lock blade 230 in the holder and secure it in three-dimensions when it has been fully mounted in the holder.

An Alternative Locking Mechanism

Figure 20:
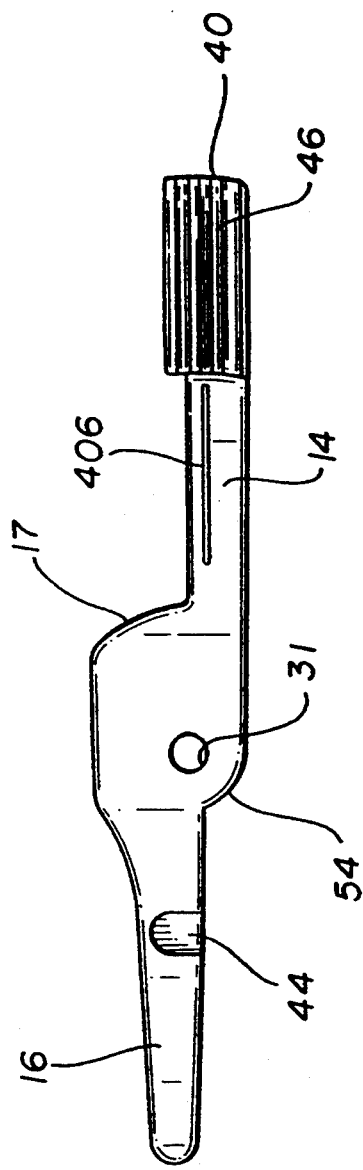
FIG. 20 is a side elevational view of a rotatable handle portion on a prefered holder of the invention showing a locking channel.
Figure 21:
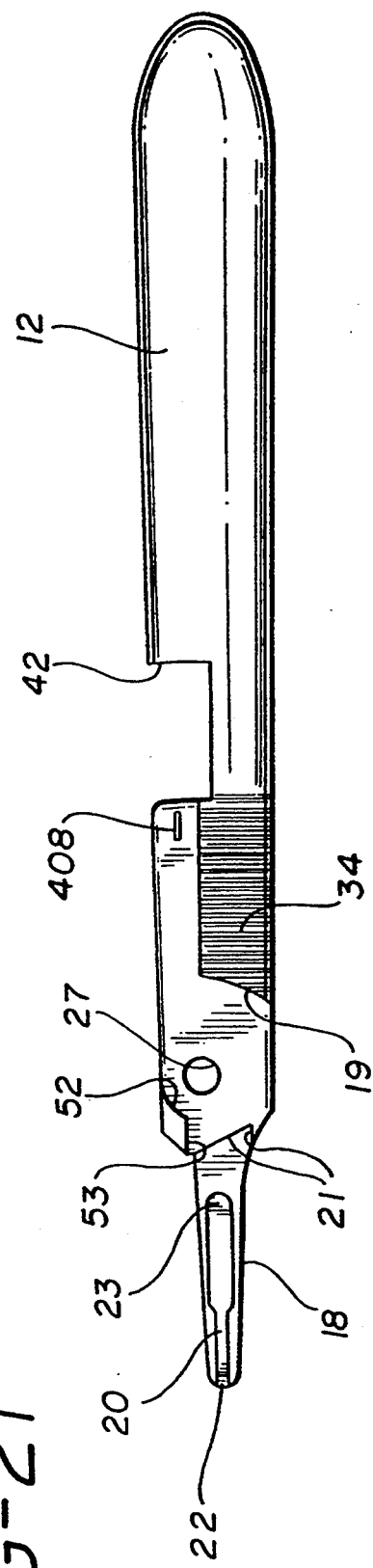
FIG. 21 is a side elevational view of a fixed handle portion on a prefered holder of the invention showing a locking protrusion that mates with the locking channel shown in FIG. 20, when the holder is in a closed position.

An alternative locking mechanism for a surgical blade holder of the present invention is shown in FIGS. 20 and 21.

FIG. 20 shows a side elevational view of rotatable handle portion 14 of the surgical blade holder having a locking channel 406 that forms a part of the alternative locking mechanism. Note that elements of handle portion 14 similar to elements in the handle portion shown in FIG. 4 are identified using the same reference numbers. Rotatable handle portion 14 in FIG. 20, however, does not include locking extension 26 shown in FIG. 4.

The alternative locking mechanism also includes locking protrusion 408 on fixed handle portion 12, as shown in FIG. 21. Locking protrusion 408 is positioned on fixed handle portion 12 so to mate with locking channel 406 on rotatable handle portion 14, when the device is in a closed position. Again, the elements of fixed handle portion 12 in FIG. 21 in common with elements in the fixed handle portion shown in FIG. 4 are identified using the same reference numerals.

As with the blade holder shown in FIGS. 1-6, when portions 12 and 14 are locked in the closed position using the alternative locking mechanism, rotary movement is prevented and the blade is locked securely in the blade receiving area. In addition, it should be understood that the blade receiving area shown in FIG. 21 is merely exemplary and could be replaced with any of the blade receiving areas shown in FIGS. 15-19 or equivalents thereof.

While the forms of apparatus herein described constitute preferred embodiments of the invention, it is to be understood that the invention is not limited to these precise forms, and that changes may be made therein without departing from the scope of the invention which is defined in the appended claims.

What is claimed is:

1. A combination surgical blade and surgical blade holder comprising:

a surgical blade and a surgical blade holder, the surgical blade having an elongated body including a first end and a second end, said elongated body having opposed side edges extending from the first end to the second end wherein the second end defines an angled surface for engaging the surgical blade holder, a blade cutting edge extending along one of the opposed side edges from a point intermediate the first and second ends to the first end, and a tab extending from the body of the blade; and the surgical blade holder having an elongated fixed body portion including a distal end and a proximal end, the fixed body portion having a blade receiving area at the distal end for receiving the blade and a handle gripping area at the proximal end, the blade receiving area having a depression for receiving the tab of the blade and a rear mating surface for mating with the angled surface of the blade, a pivot point on the fixed body portion between the distal end and the proximal end adjacent the blade receiving area, and an elongated rotatable body portion that is rotatable around the pivot point from a closed position for receiving and locking the blade in the blade receiving area to an open position for releasing the blade from the blade receiving area.

2. A surgical blade for use in a surgical blade holder comprising:

an elongated body including a first end and a second end, said elongated body having opposed side edges extending from the first end to the second end wherein the second end defines an angled surface for engaging a surgical blade holder;

a blade cutting edge extending along one of the opposed side edges from a point intermediate the first and second ends to the first end; and a tab spaced intermediate the first end and the second end and extending from said body of said blade.

3. The surgical blade of claim 2, further comprising a rib extending along the side edge opposite to the side edge having said blade cutting edge.

4. A blade holder comprising:

an elongated fixed body portion including a distal end and a proximal end, said fixed body portion having a blade receiving area at the distal end for receiving a blade and a handle gripping area at the proximal end, said blade receiving area having a depression and a rear mating surface for mating with said blade when said blade is mounted in said blade receiving area;

a pivot point on said fixed body portion between the distal end and the proximal end of the elongated fixed body portion and adjacent to and proximal to the depression in said blade receiving area; and an elongated rotatable body portion that is rotatable around said pivot point from a closed position for receiving and locking said blade in said blade receiving area to an open position for releasing said blade from said blade receiving area.

5. The blade holder of claim 4, further comprising frictional gripping surfaces on each side of said fixed and rotatable body portions for preventing said blade holder from slippage during use.

6. The blade holder of claim 4, further comprising a frictional gripping surface on a side of said rotatable body portion for urging said rotatable body portion to the open position.

7. The blade holder of claim 4, further comprising cooperating locking means on said fixed body portion and said rotatable body portion for locking said blade in said blade receiving area.

8. The blade holder of claim 7, wherein said cooperating locking means comprises:

a channel on said fixed body portion; and a protrusion on said rotatable body portion, wherein said protrusion mates with said channel when said rotatable body portion is in the closed position, thereby locking said rotatable body portion to said fixed body portion in the closed position.

* * * * *